United States Patent [19]

Hachey

[11] Patent Number: 5,245,558
[45] Date of Patent: Sep. 14, 1993

[54] COMPUTER SYSTEM FOR DISABLED USER

[75] Inventor: John P. Hachey, East Walpole, Mass.

[73] Assignee: Synergy, East Walpole, Mass.

[21] Appl. No.: 849,478

[22] Filed: Mar. 11, 1992

[51] Int. Cl.⁵ .............................................. G06F 1/00
[52] U.S. Cl. .............................................. 364/708.1
[58] Field of Search ............... 364/708, 709.01, 704, 364/705.01, 424.05; 307/73; 361/380; 361/380

[56] References Cited

U.S. PATENT DOCUMENTS

| | | | |
|---|---|---|---|
| 5,021,763 | 6/1991 | Obear | 364/708 |
| 5,033,000 | 7/1991 | Littlejohn et al. | 364/424.05 |
| 5,103,110 | 4/1992 | Housworth et al. | 307/73 |

FOREIGN PATENT DOCUMENTS 0182413  5/1986  European Pat. Off. ............ 364/708

OTHER PUBLICATIONS

Flyer from Access to Learning: Integrating Adaptive Technology into the Classroom, Presentation, Technology and Persons with Disabilities, California State University, Los Angeles, Calif., Mar. 20-23, 1991.

D. Russell, "Access To Independence: Integration Through The Use Of Technology", Conference Proceedings World Congress on Technology, Dec. 1-5, 1991, Arlington, Va., vol. II, pp. 339-346.

*Primary Examiner*—Long T. Nguyen
*Attorney, Agent, or Firm*—Hamilton, Brook, Smith & Reynolds

[57] ABSTRACT

A Computer System is designed to meet the needs of individuals with physical disabilities who use battery-powered wheelchairs. To accommodate these individuals' specialized needs, this computer system provides the infrastructure of a standardized Bus in a format that also incorporates specialized features. Providing a standardized Bus allows the use of cards which perform functions which otherwise would need to be met by adding external devices. Use of a standardized Bus also allows for ease of upgrade and repair. This standardized bus is then incorporated into a specialized format: 1) it has the capability to be powered by a portable power source, such as a power wheelchair's battery, so that it is consistently available in all environments and under a variety of conditions; 2) each component is able to be effectively mounted to a wheelchair in the optimal position for a specific individual; 3) all of the components are durable and weather resistant; 4) it is able to be maintained and operated throughout the day without requiring any assistance from an able-bodied individual for activities such as using the computer's on, off or reset controls; 5) its components are easily accessible, allowing for ease of upgrade and/or repair; and 6) the ports are redefinable, allowing for any combination required.

13 Claims, 3 Drawing Sheets

COMPUTER SYSTEM FOR DISABLED USER

BACKGROUND OF THE INVENTION

The Need for This Invention

Many individuals with physical disabilities are unable to effectively:
walk independently
speak
use their hands to:
handwrite
type
turn pages in a book
access papers and files
operate appliances, such as a telephone, stereo, microwave, light switch, printer In order to live, learn and work productively, people need to be able to perform these functions in a variety of settings and in a timely and socially appropriate manner. For instance, at work a person often needs to take notes and retrieve information during meetings and in settings away from his own office. He needs to converse with colleagues and use the telephone. To research information, he needs to be able to simultaneously retrieve information from numerous books and files, take notes and write reports. Individuals with disabilities need technology that will allow them to engage in these activities despite physical limitations.

Current Technologies Attempting to Address This Need

People have attempted to meet the numerous needs of individuals with disabilities using a variety of discrete technologies, each for a specified purpose.
These technologies have included:
manually powered wheelchairs
battery powered wheelchairs
laptop computers to write, to retrieve information, and to "speak"
adaptive input devices for accessing computers when use of a keyboard is not physically possible
speech synthesizers to produce "speech" for communication
environmental control units (ECUs) to operate appliances via adaptive inputs.

For the individual physically unable to walk, speak or use his hands effectively, the state-of-the art effort to meet his needs has been to mount a laptop (or "notebook") computer onto his wheelchair, and then attach other adaptive devices that he may need. Laptop computers are used rather than desktop computers since the laptop computers can be attached to a wheelchair and are battery powered.

If an individual with disabilities is unable to use the laptop computer's keyboard, an adaptive input device would be attached. One such device is the so called Headmaster, by Prentke-Romich of Wooster, Ohio, and allows the user to control his computer by moving his head. Another option for input might be a specialized keyboard with large, 1.5 inch, touch-sensitive areas instead of standard keys, such as the so called expanded keyboard, commercially available from Unicorn Engineering, Richmond, Calif.

To provide a means of communication for those individuals unable to speak, a speech synthesizer has been added to the laptop computer. One option has been to install a small specialized card into the modem port of certain laptops. This option provides speech output in a manner that is space efficient but not of the highest quality and available only in a male voice.

The only options currently available for high quality male, female, or child-like speech output are the Voice Mate speech synthesizer commercially available from Digital Equipment Corporation, Maynard, Mass. and The Institute on Technology, Boston, Mass. or the Realvoice PC commercially available from Adaptive Communication Systems, Pittsburgh, Pa. Both of these synthesizers are discrete units that must be separately attached to the wheelchair, in addition to the laptop computer. Also they require their own batteries which last only eight hours before needing to be recharged.

To operate appliances, such as a television or light switch, individuals have been provided with Environmental Control Units (ECUs) which they can control via their computer. In order to do this using a portable computer, such as a laptop, an individual would need to use an ECU such as the Serial Relax, commercially available from Technical Aids & Systems for the Handicapped, Inc. (TASH), Markham, Ontario, Canada, which is compact, powered by long-lasting batteries and does not need to be hard-wired to the items it controls.

The Serial Relax can be used to operate any infrared-controlled device, such as the remote control unit of a television. It also can operate non-infrared controlled devices, such as light switches, when a device such as the X-10 Controller is used as an interface between the Serial Relax and the X-10 Powerhouse. The X-10 Powerhouse is hard-wired to the item being controlled via the house wiring.

Limitations of These Current Technologies

The use of laptop computers combined with various peripheral devices to meet the needs of individuals with disabilities has met with a number of limitations.

Upgrading: A limitation individuals have experienced with laptop computers is in upgrading components as technology advances. When using a laptop, individuals are either unable to upgrade certain components or are required to upgrade by using proprietary components. For instance, if a laptop's processor becomes outdated, the user cannot upgrade it but must replace the entire computer. In contrast, users of desktop computers are able to update their computer by replacing components, such as a hard drive or mother board, which are standard commodity items.

Similarly, if a person wants to increase the memory (RAM) available within their laptop, they need to purchase a proprietary RAM card, which is costly. In contrast, users of desktop computers can increase their RAM using commodity dynamic RAM, which is more cost effective.

It is particularly important for individuals who need a wheelchair mounted computer system to be able to upgrade their computer rather than replace it. Since the computer generally needs to be custom mounted to the wheelchair, it would be difficult, time consuming and costly to mount a new computer system just in order to have upgraded components.

Repair: Since laptop computers require proprietary components and are non-standardized, they are expensive and time consuming to repair. In contrast, the great majority of desktop computers can be repaired by anyone familiar with IBM-compatible computers, using standard components. It is particularly important to individuals with disabilities that repairs are made in a timely manner since they rely on their computer for daily functioning.

Availability of ports: Laptop computers have a small number of ports available. They typically offer one parallel port and one serial port. Occasionally a second serial port may be available on larger, more costly models. While this number of ports is generally sufficient for the non-disabled user, it can present considerable limitations to individuals with disabilities. For instance, a serial port is usually required for each of the following peripherals; adaptive inputs, such as a trackball or Headmaster; Environmental Control Units such as the serial Relax; and external speech synthesizers, such as the two high-quality synthesizers available. An individual would typically be unable to use more than two of these devices on a laptop computer.

Availability of cards: Laptop computers generally do not accept standard Industry Standard Architecture Bus cards and none accept NuBus cards. At best larger, heavier, more costly laptop computer models have a slot which accepts one half-size, eight-bit ISA Bus card, but not a full-size, nor a sixteen-bit card. Therefore laptop users cannot utilize more than a single half-size Bus card.

Since laptop computers do not accept Bus cards, they are unable to accommodate electrical devices that are available in card form. Therefore, an individual who requires additional electrical devices (e.g., speech synthesizer) can use these devices only as independent devices. Each independent device requires the individual to use that device's own particular set of controls (e.g., knobs, buttons) to operate it, has its own enclosure that must be independently mounted to an individual's wheelchair, and requires its own power source (e.g., batteries). This presents several difficulties for the individual with disabilities: An individual may not be able to physically operate the controls of a particular device; each device's enclosure must be attached to the user's wheelchair, thus increasing the complexity of items and wires that are attached to his wheelchair; and each device's independent power source must be recharged or replaced as needed.

For instance, for an individual desiring a high quality speech synthesizer, such as those using Dectalk speech algorithms commercially available from Digital Equipment Corporation, Maynard, Mass., two forms of this synthesizer are available. If he wants to add Dectalk quality speech output to a laptop computer, he must use the external, four-pound Voice Mate speech synthesizer (which has Dectalk speech algorithms) and attach it to his wheelchair. This external speech synthesizer not only needs to be mounted separately but it also requires use of its own set of controls and its own battery which needs to be recharged every eight hours. In contrast, if a person is adding speech output to a desktop computer, he would be able to use the Dectalk PC full-size card (which uses the same Dectalk speech algorithms) and have speech output by simply placing that card into one of the computer's full-size Bus slots without adding any external components or power source.

Another example of the difficulties associated with a limited availability of cards involves individuals who are unable to operate a standard computer keyboard and need to control their computer via voice input, using a voice recognition system. The most capable voice recognition system available today is Dragon Dictate commercially available from Dragon Systems of Newton, Mass. However, this voice recognition system requires the installation of a full-size, sixteen bit card, which a laptop computer is incapable of accepting. Therefore, this voice recognition system is unavailable to individuals using laptop computers, but is available to those using desktop computer.

Batteries: Laptop computers generally require a change of batteries every one to four hours. This results in a variety of difficulties:

- Often the person with disabilities is unable to change these batteries by himself and requires assistance every few hours from someone who knows how to change the batteries.
- Since the computer must function as the individual's voice, paper and pen, it needs to be operational throughout the day, perhaps sixteen hours at a time. Since a single battery typically lasts no more than four hours, he needs to have at least four batteries in order to use the laptop computer throughout the day. Additionally, each night, all of those batteries must be recharged, necessitating further assistance.
- Additional costs are also an issue: a battery typically sells for approximately $80–100 with four batteries totalling up to $400. Furthermore, in order to recharge more than one battery at a time, it is necessary to purchase specialized battery rechargers, which typically cost $250–400 and recharge up to four batteries at a time.

Mounting: Laptop computers are a single unit. This makes them convenient for non-disabled persons to carry. However, for individuals who use adaptive access to the computer, a single unit is more difficult to attach to a wheelchair in an effective manner. An entire laptop computer, including CPU and keyboard, must be attached to the front of their wheelchair in order for the display to be visible to the user. Even individuals who use adaptive inputs and are unable to use a standard keyboard must have the entire laptop, with keyboard, and CPU, mounted to the front of their wheelchair. For instance, an individual may require a specialized Expanded Keyboard (e.g., the Unicorn expanded keyboard by Unicorn Engineering, Inc.) with large touch-sensitive areas instead of keys, which is approximately 20"×15" in overall dimensions. It would be difficult to attach such a large keyboard to the wheelchair in an effective location when a laptop computer, complete with keyboard (which the individual cannot use) must also be attached to the front of the wheelchair.

In addition, complete laptop computers, particularly heavier models, mounted on a wheelchair in front of the user can present a safety hazard. In case of collision, the computer may become a projectile and fall on the user. Therefore, it is important to keep the weight of the items mounted to the front of the wheelchair to a minimum.

Weather resistance/durability: Laptop computers are not weather resistant, which presents limitations to a disabled user who needs his computer mounted to his wheelchair. Being mounted to the wheelchair, the computer may be exposed to weather conditions during travel. Such individuals may be physically unable to cover their computer if inclement weather arises.

On/off/reset: Laptop computers are turned on and off via buttons placed at specific locations. These buttons generally are inaccessible to an individual with limited physical dexterity. Furthermore, in instances where software locks up and keyboard commands are unsuccessful in restarting the computer, the individual needs to press a reset button, which also is usually inaccessible to him.

Efforts by Others to Address These Limitations

Individuals have attempted to alleviate some of the limitations described above in a number of ways.

One attempt has been described in an article, entitled "MiniVOCA," published in Communication Outlook, Winter 1990, 11:3, John Bryson Eulenberg and Stephen Ray Blosser at the Artificial Language Laboratory in Michigan. They describe the use of a disassembled laptop computer as part of a specialized system for individuals with disabilities who require speech synthesis for communication.

The system described used a specialized "MiniVOCA" unit which allowed for adaptive inputs and contained a DecTalkIII speech synthesizer board. The MiniVoca unit also contained specialized software for speech communication which allowed a user to select letters, words or pictures. The MiniVOCA used a disassembled laptop computer that the user could control using adaptive inputs. The laptop computers display was mounted to the front of the wheelchair and its CPU with keyboard was mounted to the rear of the wheelchair. The MiniVOCA unit was able to be powered via the user's wheelchair battery, but the laptop computer was powered by its own batteries.

While this attempt alleviated some of the difficulties involved in mounting a laptop computer to a wheelchair, it did not address all of those discussed in the previous section. The MiniVOCA contained a Dectalk III speech board and therefore users did not need to attach a separate speech synthesizer. However, the MiniVOCA unit itself became an additional component that the user needed to attach to his wheelchair. Also, although the MiniVOCA was powered by the user's wheelchair battery, the laptop computer connected to the MiniVOCA still was powered by its own battery and therefore presented those limitations created by a laptop requiring frequent battery changes. Furthermore, this attempt did not alleviate the limitations of a laptop computer in contrast to a desktop computer, such as inability to accept standard ISA Bus or NuBus cards, greater difficulty in upgrading and repairing the laptop computer, limited number of ports available and difficulty in physically accessing the on, off and reset buttons. Additionally, the MiniVOCA presented the user with another device, in addition to the laptop computer, which required specialized, proprietary parts to upgrade or repair.

SUMMARY OF THE INVENTION

Applicant began by attempting to address the need for a computer system which was modular (i.e., the screen, CPU and keyboard could each be independently mounted to a wheelchair) and had an all day power supply. This attempt involved disassembling a laptop computer (Toshiba 1200HD) and "repackaging" it so that the components could be mounted separately. Applicant also used a DC/DC converter with a customized connector so that this disassembled laptop computer could be powered by the same battery that powered the wheelchair on which it was mounted. After implementing these adaptations, applicant discovered that there continued to be several problems with this approach in meeting the particular needs of individuals with disabilities. These limitations included those resulting from using a laptop computer, rather than a computer that provides standardized Bus format, such as discussed in the prior sections.

Upon further development, applicant decided that laptop computers, even when disassembled and powered by a wheelchair battery, presented too many limitations to provide a viable solution to the technological needs of persons with disabilities.

Applicant therefore turned attention to providing the infrastructure available within computers having a standardized Bus in a format that simultaneously addresses the specialized needs of individuals with disabilities. Applicant thus developed the present invention to meet these requirements.

That is, the present invention provides the infrastructure available within computers having a standardized Bus in a format that also addresses the specialized needs of individuals who require a wheelchair-mounted computer system.

It is important to provide this infrastructure since it allows the use of cards which perform the functions that otherwise would need to be met by adding external devices, each requiring its own control interface, power source, and physical mounting to the wheelchair. Currently there are two such Busses which will accept a variety of Bus cards performing the functions of most electrical devices required by individuals with disabilities: the ISA (EISA) Bus and NuBus.

To accommodate specialized needs, the present invention provides this infrastructure in a design incorporating the following features: 1) able to be powered by a single, portable power source (e.g., a wheelchair battery) so that it is consistently available in all environments and under a variety of conditions; 2) each component is able to be effectively mounted to a wheelchair in the optimal position for a specific individual; 3) durable and weather resistant; 4) able to be maintained and operated throughout the day without requiring any assistance from an able-bodied individual for activities such as using the computer's on, off or reset controls; 5) accessible components allowing for ease of upgrade and/or repair; and 6) redefinable ports allowing for any combination of ports required.

The features of a standardized Bus which have been incorporated into the present invention include:

Accepts a Full Spectrum of Cards: The present invention computer system accepts a full range of standard Bus cards and provides a containment for these cards which is of a size adequate to accept the range of card sizes defined by Bus standards. Furthermore, the present invention computer system provides a means to mount these cards within this containment in a standardized manner.

By accepting a full spectrum of cards, the present invention computer system allows the use of devices that are available in card form, such as speech synthesizers (e.g., the DecTalk PC by Digital Electronic Corporation of Maynard, Mass.), adaptive inputs (e.g., Dragon Dictate by Dragon Systems of Newton, Mass.), stereo, television and video receivers (e.g., Desktop Stereo and Desktop TV/VG1 by Personal Computing Tools of Los Gatos, Calif.) Since Bus cards are controlled by the computer system's Bus, an individual using a control interface to control their computer via an adaptive input device (e.g., a head-controlled switch) is able to use that same adaptive input to control any electronic device that is in card form and attached to the computer's Bus. In this way, an individual whose physical disability precludes his ability to access the variety of controls (e.g., buttons, knobs) on external electrical devices is able to use a single accessible control interface to control these devices when they are available in card form.

Furthermore, the capability to make use of devices available in card form minimizes the number of external devices that must be individually mounted onto a user's wheelchair. This capability also allows for devices used in card form to be powered by a single power source. The prototype ISA Bus model accepts eight cards, each of which can be up to sixteen bits and full size.

Provides Numerous Ports: Through the addition of Bus cards, the present invention computer system provides numerous ports, enabling the addition of any number of internal or external devices that may be necessary. The prototype ISA Bus model provides eleven standard ports; if needed, up to another seventy-five ports could be added via additional Bus cards. A NuBus model would provide at least twenty-five ports, including SCSI, serial, ADB, audio, video. If needed, additional ports could be added via additional Bus cards.

Standard Components: With the exception of the display and power supply, all components of the present invention are standard commodity items. They are readily available from a variety of generic sources and therefore can be easily replaced or upgraded.

The ability to easily upgrade or repair a computer system is particularly essential for individuals requiring a wheelchair-mounted computer system. Such a computer system must be custom mounted to an individual's wheelchair to accommodate his particular physical characteristics as well as the specific configuration of his wheelchair. Custom mounting is both time consuming and expensive. This puts a premium on the capability of a computer system to be easily repaired or upgraded. Additionally, these individuals typically depend on their computer for essential activities, such as "speaking," or "writing." Therefore, it is, essential that the time period that they cannot use their computer is minimized as much as possible.

The specialized format of the present invention which specifically addresses the needs of individuals requiring a wheelchair-mounted computer system includes:

A Single Portable Power Source:

Portable power sources (e.g., batteries) do not provide the standard or stable voltages required to power a computer. Through the use of a DC/DC converter the nonstandard and fluctuating voltages from a portable power source (e.g., batteries) are converted to the specific and stable voltages required by a computer. Through the use of such a DC/DC converter, an individual who uses a battery-powered wheelchair can make use of the same battery which serves to power his wheelchair to power his computer.

That is, the present invention computer system provides a standardized Bus which accepts a full spectrum of cards, along with a standardized means to access the nonstandard, fluctuating power provided by a portable power source, such as wheelchair batteries. The invention computer system converts the voltages of a portable power source to the specific, stable voltages that can power the entire computer system as well as any additional electrical devices, such as a variety of alternative input devices (e.g., the Headmaster, by Prentke-Romich). In this way, devices that otherwise would need to be attached, accessed or powered independently can be provided internally (in card form) or attached externally and be accessed and powered by the invention computer system.

Modular Design: The major components of the invention computer system are: 1) a flat panel display; 2) an enclosed unit or assembly, containing the CPU, hard drive and floppy drive; 3) keyboard or other input device. Each of these components can be attached to the wheelchair independently, in any location. For instance, if a user accesses the computer via a single switch, he can mount just the computer's flat screen in front of him, the switch in an optimal location for his specific physical characteristics (e.g., on his wheelchair headrest) and the CPU enclosure on the back of the wheelchair. If he is unable to use a keyboard, it does not need to be attached.

Weather Resistant Design: The present invention computer system is designed to be weather resistant, so that all of the components are protected from the weather exposure that occurs during travel in a wheelchair.

Durable, Industrial-Grade Connectors: All connectors are weathertight, durable, and attach securely. Therefore these connectors are less likely to be damaged or disconnected when subjected to the weather exposure, bumping and jarring that occurs during travel in a wheelchair.

Accessibility of Power-on, Power-off and Reset Switches: The present invention computer system provides three distinct switch outlets which accommodate any single ability switch which has a ⅛ inch miniature plug. These switches function to: 1) turn the computer on, 2) turn the computer off, and 3) reset the computer. In this way, individuals with disabilities are able to independently control these functions regardless of their physical capabilities.

Accessible Components: To further enhance ease of repair and upgrade, the invention computer system is "packaged" in a case which is hinged with latches that are easily opened and closed. Therefore, the CPU components are easily accessible for upgrade and repair by simply unlatching the case and lifting the hinged lid.

Redefinable Ports: Each of the three external connectors on the invention computer system can be re-defined by the user to be any desired type of port, such as parallel, serial, game, floppy, power, SCSI. Additionally, each of these connectors can be configured to accommodate multiple ports.

In a preferred embodiment of the present invention, a computer system for a disabled wheelchair user is comprised of a converter coupled to the wheelchair battery, a processor assembly coupled to the converter and I/O devices (e.g., a monitor and an input device). The converter is coupled to the wheelchair battery to convert power from the battery to the voltages necessary to power the processor assembly. To that end, the wheelchair battery serves as a power source for the computer system. The processor assembly includes a digital processor coupled to a standard Bus having a plurality of nodes for receiving accessory Bus cards. The monitor is coupled to the processor assembly and has a display for displaying output from the digital processor. The monitor also has at least one connector for connecting the input device to the processor assembly through the monitor. So connected, the input device provides user input to the digital processor. In response, the digital processor accesses the necessary memory areas (internal and/or external) and/or Bus cards and generates output transmitted to the monitor for driving the display.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

The ISA Bus format is the embodiment illustrated in these drawings and is intended to be a non-limiting illustration of the invention. However, the same principles and set of conditions apply to other Bus formats, such as NuBus. Likewise, a wheelchair battery is the embodiment power source illustrated in these drawings and is intended to be a non-limiting illustration of the invention. However, the same principles and set of conditions apply to other portable power sources, such as batteries dedicated to powering the computer system, mounted internal or external to the computer system's case.

DETAILED DESCRIPTION OF THE PREFERRED EMBODIMENT

Figure 1:
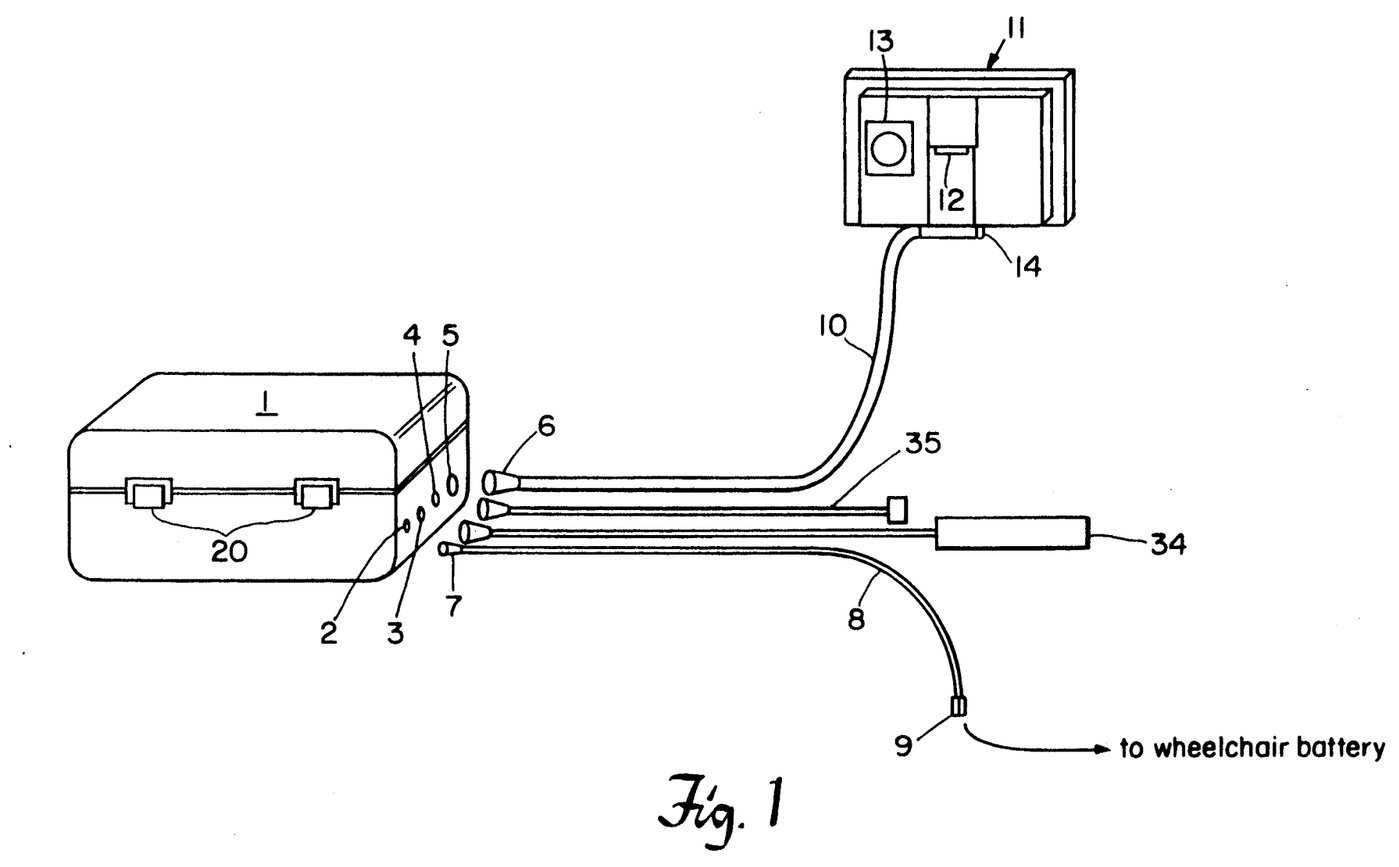
FIG. 1 is a schematic view of the components of the preferred embodiment of the present invention.

FIG. 1 illustrates the components of an embodiment of the present invention computer system. The CPU assembly 1 has an aluminum case-like housing which serves as a shield both to protect the system from the environment and to contain Radio Frequency Interference (RFI). The aluminum case-housing of CPU assembly 1 also serves as a heat sink for the power supply and other internal components.

There are four connectors 2, 3, 4 and 5 on one (i.e., the right) side of the CPU assembly 1. The power connector 2 accepts a power cable connector 7 which is at one end of the power cable 8. At the opposite end of the power cable 8 is the power cable plug 9 which connects to the battery recharger port of any standard wheelchair battery.

The external floppy disk drive connector 3 connects to an external 3.5 inch or 5.25 inch floppy disk drive 34. The parallel port connector 4 connects to any standard parallel device via an adapter cable 35. An example of such a parallel device is a printer. The monitor connector 5 connects to the monitor cable connector 6 at one end of the monitor cable 10. The monitor cable 10, extends from the monitor 11 and connects to the CPU assembly 1 at the monitor connector 5.

All connectors, 2, 3, 4, 5, 6, 7 are weathertight, durable, and attach securely. Therefore these connectors are less likely to be damaged or disconnected when subjected to the weather exposure, bumping and jarring that occurs during travel in a wheelchair.

Figure 2A:
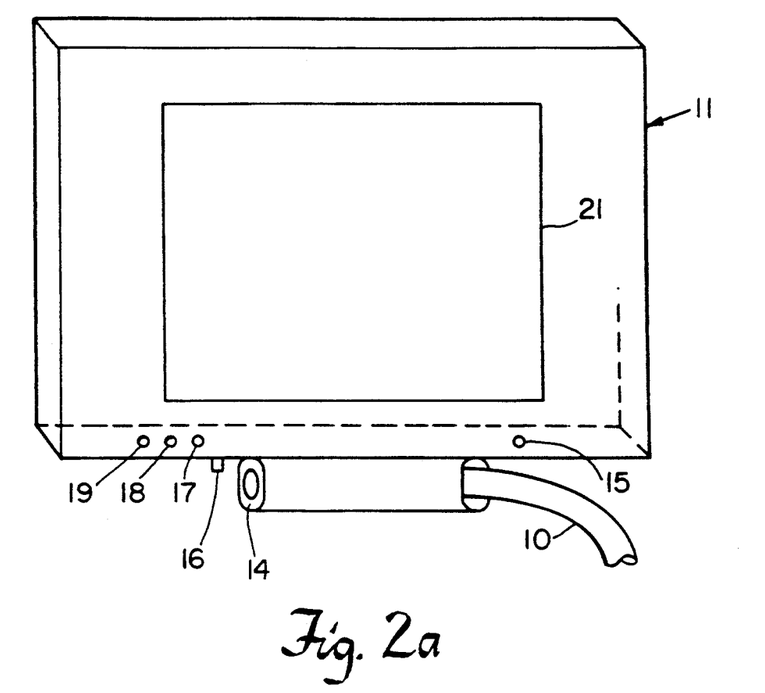
FIG. 2a and FIG. 2b are front and back views, respectively, of the monitor of the embodiment of FIG. 1.
Figure 2B:
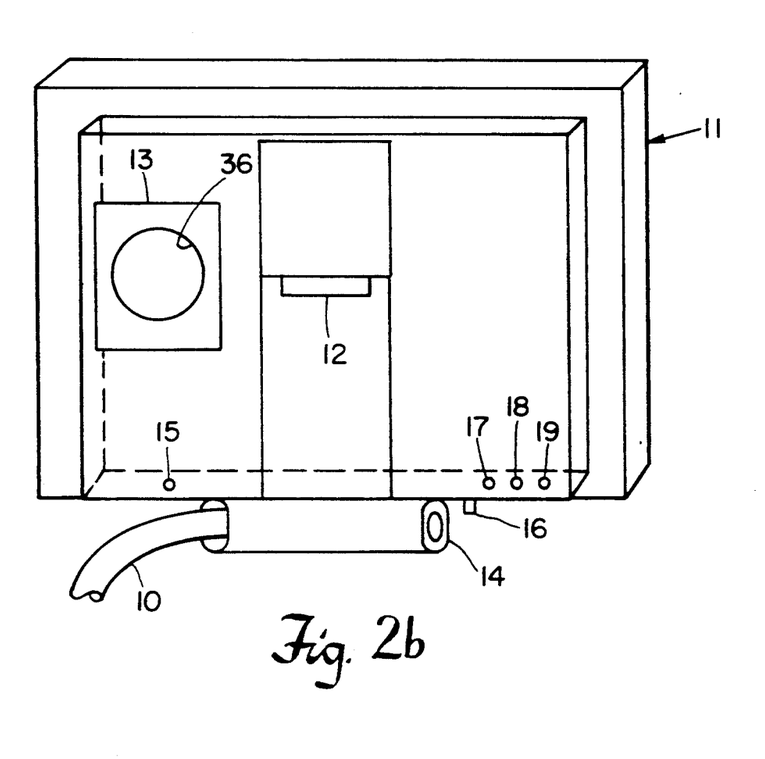

In FIG. 2a and FIG. 2b, the monitor cable 10 carries power and signals for the following: LCD flat panel display 21, access connector 12 (for connecting various input, peripheral or other devices), keyboard port 14, audio output speaker 13, external audio connector 15, reset switch connector 17, power-on switch connector 18 and power-off switch connector 19. The capability of this monitor cable 10 to carry multiple lines minimizes the number of individual cables otherwise required to serve those various functions. Utilizing a single cable to carry multiple lines simplifies the task of connecting and disconnecting cables in order to remove or attach the computer to a wheelchair. Utilizing a single cable to carry multiple lines also minimizes the number of cables and wires that need to surround an individual when he is seated in his wheelchair.

The access connector 12 and keyboard port 14 are both located at the monitor case 11 to optimize the mounting of an individual's input device to his wheelchair. An input device used to access the present invention computer system would be either a keyboard or an adaptive input device (e.g., a serial device such as a trackball) mounted to the wheelchair in front of the user. Therefore, when the present invention computer system is mounted to a wheelchair, both the monitor 11 and input device (e.g., keyboard or adaptive input device) are mounted to the front of the wheelchair and the CPU assembly 1 is mounted to the back (side or underside and the like) of the wheelchair where there is space to easily accommodate it. Mounting is optimized when the input device is attached near the monitor 11 so that both the input device and the monitor case 11 are located in the front of the wheelchair. Otherwise, one would have to run cables around from the input device mounted near the front of the wheelchair to the back of the wheelchair where the CPU assembly 1, with connectors, would be mounted.

Monitor 11 is of general construction, e.g., molded plastic or otherwise formed housing with a planar frontal surface, back panel area and surrounding sides for enclosing or holding electronic components. Included in the electric components are standard audio speaker 13 parts, common electronic parts for supporting display 21 and wiring coupling connectors 17, 18, 19 to monitor cable 10. Further, a contrast adjustment knob 16, external audio connector 15, reset switch connector 17, power-on switch connector 18 and power-off switch connector 19 are all located on the underside of the monitor 11 and thus are minimally exposed to the elements, such as weather and dust. The audio output speaker 13 is made weather resistant by use of a gore-tex membrane 36, which is sealed to the monitor 11 behind the opening for the audio output speaker 13. The attachment of the flat panel display 21 to the frontal surface of monitor 11 is made weathertight by a silicone seal around the display, between the display 21 and the monitor 11.

The contrast adjustment knob 16 provides for adjusting the contrast of the LCD flat panel display 21. The configuration, functioning and connection to the monitor of the contrast adjustment knob 16 is by common methods and means. Also, it is noted that display 21 may be of the plasma, multi-synch EL or LCD type. The reset switch connector 17, power-on switch connector 18 and power-off switch connector 19 each accept any standard single ability switch, allowing individuals with any degree of physical disability to independently turn their computer on and off and reset their computer using single ability switches placed in any location optimal for that individual. With such switches connected to connectors 17, 18, 19, operation is as follows. Upon activation by anyone of such single ability switches, signals are sent to the monitor 11 through the respective connector 17, 18, 19. In turn, the signals travel through monitor 11 to monitor cable 10 which carries the signals to CPU assembly 1 (FIG. 1). The signals are received through monitor connector 5 of CPU assembly 1, and thereafter are processed by the CPU at 28 (FIG. 3).

Connectors 3, 4, 12, 14 each are able to be reconfigured within the CPU assembly 1 as any I/O port within the limits of the number of lines leading to the connector. Connectors 3, 4 each provide 28 pins with 28 corresponding lines. The access connector 12 provides 25 pins with 24 corresponding lines. The keyboard connector 14 provides 5 pins with 4 corresponding lines.

Any of the connectors 3, 4, 12 can be reconfigured, for instance, to be a parallel, serial, game or power port. This allows individuals to access any combination of ports which they may require for their specialized needs. As an example, the access connector 12 is typically configured to be a serial port but can be redefined in the CPU assembly 1 to be a parallel port or game port. To change the access connector 12 from a serial port to a parallel port, one would simply: 1) attach a standard male-to-male gender changer to the corresponding connector in the CPU (a 25 pin D female connector which is attached to monitor cable connecter 6 inside the CPU), and 2) attach a standard female-to-female gender changer to the access connector 12 so that it accepts a standard female parallel cable. This is possible because pins 1–24 of both the access connector 12 and its corresponding connector in the CPU assembly 1 are all wired straight through from the access connector 12 to its corresponding connector in the CPU assembly 1. Therefore, it is straightforward to attach many other combinations of ports. With custom made cables, the access connector 12 could be reconfigured from a serial port to: a game port, up to three (3) serial ports, or a power port providing power for small peripheral devices.

Figure 3:
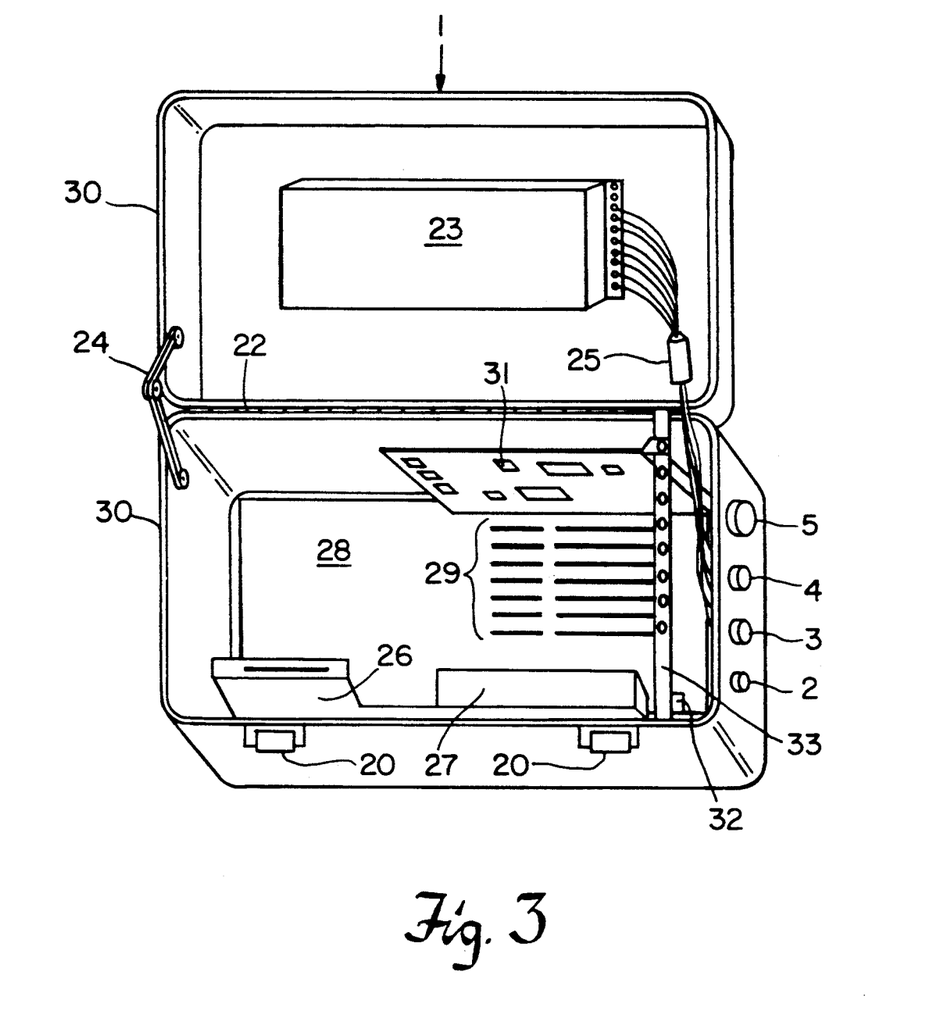
FIG. 3 is a schematic view of the inside of the assembly which contains the Central Processing Unit (CPU) in the embodiment of FIG. 1.

In FIG. 3, the internal components of the CPU assembly 1 are easily accessed via two latches 20 and hinge 22 of the CPU assembly housing; the cover prop 24 holds the assembly housing open. This provides easy access to the floppy disk drive, CPU and other components located within the case-like housing which may require repair or upgrade. An O-ring gasket 30 seals the case-like housing weathertight so that it is protected from the weather exposure that occurs during travel in a wheelchair.

A DC/DC power supply 23 is connected to the wheelchair battery through power connector 2. DC/DC power supply 23 converts twenty-four (24) volt wheelchair battery power to +5 volt, +/−12 volt power required by the computer. Outputs from DC/DC power supply 23 are coupled to connectors 2, 4 and 5 and the mother board 28 for supporting external floppy drive 34, peripheral devices, monitor 11 and CPU assembly internal components. In this way, the computer infrastructure, powered by the wheelchair battery, is able to provide a standardized power source for additional electrical devices in the form of ISA Bus cards, such as adaptive input devices or speech synthesizers that otherwise would require their own, separate, power source, weathertight enclosure, and attachment to the wheelchair. A ferrite bead 25 removes radio frequency interference from DC/DC power supply inputs and outputs.

A standard 1.44 megabyte, 3.5 inch floppy disk drive 26 allows for loading software and data onto the hard drive 27, which is the mass storage device for the CPU. The hard drive 27 is any standard hard drive which is half-height, 3.5 inch or smaller. Thus the hard drive can contain any number of megabytes as available in these standard hard drives (currently up to a gigabyte). The motherboard 28 contains the digital processor, DRAM memory and eight (8) ISA Bus card slots 29. The motherboard can be any standard "baby" size motherboard (i.e., 8.75 inches by 13.0 inches). Thus any standard processor type (e.g., 286, 386, or 486) and speed is available. Similarly, the amount of DRAM memory that can be placed on the motherboard (e.g., 1 megabyte up to 128 megabytes) is determined by the motherboard chosen. The DRAM memory and processor are coupled to the motherboard 28 by common methods and means.

The capability of the present invention computer system to accept standard components allows it to be readily repaired or upgraded. This is particularly advantageous for individuals requiring a wheelchair-mounted computer system, since they rely on their computer for "speech," "writing," and productivity and thus need to minimize the time that the computer is unavailable. Also, these individuals need their computer system to be custom-mounted to their wheelchair and thus must minimize the need to replace a computer system since a new system again would need to be custom-mounted.

In a preferred embodiment, the motherboard accepts up to eight full-length, sixteen-bit ISA Bus cards, placed in the ISA Bus card slots 29. For illustration, one card 31 is drawn in FIG. 3. In a preferred embodiment, ISA Bus cards (e.g., 31) contain functions for floppy drive controller, IDE hard drive controller, two (2) serial ports, a parallel port, two (2) game ports, a flat panel display driver, and a CRT port. The capability to accept a full spectrum of ISA Bus cards allows the use of devices that are available in card form, such as speech synthesizers (e.g., Dectalk PC, by Digital Equipment Corporation), speech input processors (e.g., Dragon Dictate, by Dragon Systems), or Spread Spectrum RF network cards.

A bracket 33 accepts screws to retain the ISA Bus cards (e.g., 31) and stabilize them during travel on a wheelchair. A power relay 32 allows power to the computer to be turned on and off via any two (2) separate single ability switches. Signals from these switches are received through monitor connector 5 as previously described and are transmitted to power relay 32 through motherboard 28.

According to the foregoing, operation of the present invention computer system is then summarized as follows. Initial power is received from a portable power source (e.g., a power wheelchair's battery) through power cable 8 at power connector 2 of the CPU assembly 1 (FIG. 1). An input lead from power connector 2 to DC/DC power supply 23 transfers the received wheelchair battery power to power supply 23. There the power is converted to desired voltage and subsequently output to motherboard 28 and connectors 3, 4, 5. The power output through connectors 3, 4, 5 supports external floppy drive 34, peripherals connected to adapter cable 35 and monitor 11 (FIG. 1). That is, user activated switches/keys of input devices (coupled at keyboard port 14 and/or access connector 12 of monitor 11) produce signals that are carried through monitor cable 10 (FIG. 2) to motherboard 28 via monitor connector 5 (FIG. 3). At the motherboard 28 (FIG. 3), the signals are carried by a standard microcomputer bus, such as ISA, NuBus or the like, to (and from) the processor. The processor responds and access internal memory (via hard drive 27 or floppy drive 26), external floppy memory (via connector 3 and external floppy drive 34) and bus cards 31 as needed. The processor subsequently outputs signals through monitor connector 5 and monitor cable 10 to drive display 21 and audio output speaker 13 (FIG. 2), and/or through parallel port connector 4 and adapter cable 35 (FIG. 1) to drive a printer or the like.

While the invention has been particularly shown and described with reference to a preferred embodiment thereof, it will be understood by those skilled in the art that various changes in form and details may be made therein without departing from the spirit and scope of the invention as defined by the appended claims. For example, the standard bus of the motherboard may be ISA, EISA, Microchannel or NuBus. Similarly, the portable power source may be wheelchair batteries or batteries dedicated to powering the system and mounted internal or external to the CPU case.

I claim:

1. A modular computer system for a disabled user having (i) a wheelchair and (ii) a portable power source, the computer system comprising:
   a converter coupled to the portable power source to convert power from the portable power source to a desired voltage such that the portable power source serves as an initial power source;
   a processor assembly coupled to the converter in a manner such that the converter provides the desired voltage to the processor assembly to power the processor assembly, the processor assembly including a digital processor coupled to a Bus having a plurality of nodes for receiving standard sized accessory Bus cards;
   a housing for holding the converter and processor assembly together to form a first unit;
   a monitor coupled to the processor assembly, the monitor being a second unit separate from the first unit, and having: (i) a display for displaying output from the digital processor, and (ii) at least one connector for connecting an input device to the processor assembly through the monitor; and
   an input device connected to the connector of the monitor for providing user input to the digital processor, the digital processor being responsive to the input device and generating output transmitted to the monitor for driving the display, the input device being a third unit separate from the first and second units, such that the computer system is modular and powered by the portable power source.

2. A computer system as claimed in claim 1 wherein the monitor further includes a means for mounting the monitor to the wheelchair in a location spaced from the first and third units.

3. A computer system as claimed in claim 2 wherein the housing is case-like having two halves hinged together along one side and latching together at an opposite side in a manner that is weathertight.

4. A computer system as claimed in claim 1 wherein the Bus of the processor assembly is of the Industry Standard Architecture (ISA) type.

5. A computer system as claimed in claim 1 further comprising a plurality of Bus cards for coupling to the nodes of the Bus in the processor assembly, the Bus cards being supported by the digital processor to provide at least one of speech synthesizing, mass storage and adaptive input.

6. A computer system as claimed in claim 1 wherein the monitor further includes an audio output speaker for providing audio output from the processor assembly.

7. A computer system as claimed in claim 1 wherein the monitor further includes as a connector an access connector which is reconfigurable from a serial port to one of a game port, multiple serial ports and a power port for connecting peripheral devices to the processor assembly.

8. A computer system as claimed in claim 1 further comprising a multiplicity of reconfigurable connectors for connecting external devices to the processor assembly.

9. A computer system as claimed in claim 1, wherein the monitor, is weathertight.

10. In a portable computer system for a disabled user in a wheelchair having: (i) a digital processor coupled to a standard bus, (ii) a display monitor unit coupled to the digital processor, and (iii) an input device unit coupled to the digital processor, the improvement comprising:
    a powered wheelchair battery; and
    a converter coupled between the wheelchair battery and the digital processor, display monitor and input device units to convert voltage useable by the digital processor, display monitor and input device units, such that the digital processor, display monitor and input device units are effectively powered by the wheelchair battery; and
    a housing for holding together the converter and digital processor as a separate unit from the display monitor unit, input device unit, and the battery, such that the computer system is modular.

11. A computer system for a disabled user having a wheelchair and a portable power source, the computer system comprising:
    a converter coupled to the portable power source to convert power from the portable power source to a desired voltage such that the portable power source serves as an initial power source; and
    a processor assembly coupled to the converter in a manner such that the converter provides the desired voltage to the processor assembly to power the processor assembly, the processor assembly including a digital processor coupled to a standard Bus, the processor assembly and the converter forming a single unit separate from the portable power source, such that the computer system is modular and powered by the portable power source.

12. A computer system as claimed in claim 11 further comprising:
    a housing for holding the processor assembly such that full-size cards are received by the Bus and contained by the housing.

13. A computer system as claimed in claim 11 further comprising:
    a monitor coupled to the processor assembly, the monitor having: (i) a display for displaying output from the digital processor; and
    an input device connected to one of the monitor and processor assembly for providing user input to the digital processor, the digital processor being responsive and generating output transmitted to the monitor for driving the display.

* * * * *